US005112690A

United States Patent [19]
Cohen et al.

[11] Patent Number: 5,112,690
[45] Date of Patent: May 12, 1992

[54] LOW HYDROHEAD FIBROUS POROUS WEB WITH IMPROVED RETENTIVE WETTABILITY

[75] Inventors: Bernard Cohen, Berkeley Lake; Michael T. Morman, Alpharetta, both of Ga.

[73] Assignee: Kimberly-Clark Corporation, Neenah, Wis.

[21] Appl. No.: 608,103

[22] Filed: Nov. 1, 1990

[51] Int. Cl.⁵ ............................................. B05D 3/06
[52] U.S. Cl. ................................. 428/411.1; 427/40; 427/41
[58] Field of Search ................... 427/39, 41, 40; 428/411.1

[56] References Cited

U.S. PATENT DOCUMENTS

| | | | |
|---|---|---|---|
| 2,109,333 | 9/1938 | Formhals | 18/8 |
| 2,116,942 | 5/1938 | Formhals | 18/8 |
| 2,123,992 | 7/1938 | Formhals | 18/8 |
| 2,158,416 | 5/1939 | Formhals | 18/8 |
| 2,160,962 | 6/1939 | Formhals | 18/8 |
| 2,168,027 | 8/1939 | Gladding | 18/8 |
| 2,187,306 | 1/1940 | Formhals | 18/8 |
| 2,265,742 | 12/1941 | Norton | 18/8 |
| 2,293,165 | 8/1942 | Norton | 18/8 |
| 2,336,745 | 12/1943 | Manning | 18/8 |
| 3,111,471 | 11/1963 | Evans et al. | 204/168 |
| 3,135,676 | 6/1964 | Rothacker | 204/168 |
| 3,245,896 | 4/1966 | James, Jr. | 204/168 |
| 3,281,347 | 10/1966 | Winder | 204/168 |
| 3,319,309 | 5/1967 | Owens | 28/1 |
| 3,338,992 | 8/1967 | Kinney | 264/24 |
| 3,369,982 | 2/1968 | Wood | 204/168 |
| 3,376,208 | 4/1968 | Wood | 204/168 |
| 3,387,326 | 6/1968 | Hollberg et al. | 18/8 |
| 3,436,797 | 4/1969 | Graf et al. | 28/1 |
| 3,471,597 | 10/1969 | Schirmer | 264/25 |
| 3,481,005 | 12/1969 | Owens et al. | 19/156.4 |
| 3,490,115 | 1/1970 | Owens et al. | 28/1 |
| 3,496,255 | 2/1970 | Erxleben et al. | 264/24 |
| 3,565,979 | 2/1971 | Palmer | 264/24 |
| 3,578,739 | 5/1971 | George | 18/8 |
| 3,689,608 | 9/1972 | Hollberg et al. | 264/24 |
| 3,692,653 | 9/1972 | Drelich et al. | 204/165 |
| 3,754,117 | 8/1973 | Walter | 219/383 |
| 3,880,966 | 4/1975 | Zimmerman et al. | 264/25 |
| 3,973,068 | 8/1976 | Weber | 428/198 |
| 4,024,038 | 5/1977 | Luc | 204/168 |
| 4,197,267 | 4/1980 | Gustavsson | 264/24 |
| 4,208,366 | 6/1980 | Kinney | 264/24 |
| 4,340,563 | 7/1982 | Appel et al. | 264/518 |
| 4,375,718 | 3/1983 | Wadsworth et al. | 29/592 E |
| 4,535,020 | 8/1985 | Thomas et al. | 428/131 |
| 4,623,438 | 11/1986 | Felton et al. | 204/168 |
| 4,663,220 | 5/1987 | Wisneski et al. | 428/221 |

FOREIGN PATENT DOCUMENTS

| | | |
|---|---|---|
| 49-035692 | 4/1974 | Japan . |
| 58-180656 | 10/1983 | Japan . |
| 60-094664 | 5/1985 | Japan . |
| 60-235845 | 11/1985 | Japan . |
| 61-146878 | 7/1986 | Japan . |
| 61-168631 | 7/1986 | Japan . |
| 69004251 | 3/1987 | Japan . |
| 63-211375 | 7/1988 | Japan . |
| 63-042016 | 8/1988 | Japan . |
| 1195221 | 6/1970 | United Kingdom . |

OTHER PUBLICATIONS

Catoire, et al., "Physico-chemical modifications of superficial regions of low-density polyethylene (LDPE) film under corona discharge", Polymer, vol. 25, pp. 766 et seq., Jun., 1984.

(List continued on next page.)

Primary Examiner—Bernard Pianalto
Attorney, Agent, or Firm—Joseph P. Harps

[57] ABSTRACT

A method of treating a low hydrohead fibrous porous web material to increase its retentive wettability, by at least about 50%, as compared to untreated low hydrohead web material, is disclosed. The increase in retentive wettability is evidenced by the increase in the average number of runoff tests that the treated web material can sustain without unacceptable runoff is disclosed.

The invention is also directed to products prepared or preparable by the process.

24 Claims, 3 Drawing Sheets

PERCENT INCREASE IN NUMBER OF RUN-OFFS

OTHER PUBLICATIONS

Goeller et al., Urination in the First Three Years of Life, Nephron, 28:174–178 (1981).
Griffin, W. C., Classification of Surface Active Agents by "HLB", J. Soc. Cosmetic Chemists, 317–326 (1949).
"A Study of Polyolefin Films and Yarns Under Corona Discharge", Catorie, et al., pp. 457 and 469.
"Modification of polypropylene film with corona discharge treatment—improvement of bondability and surface analysis by ESCA", *Shizuoka-ken Kogyo Gijutsu Senta Kenkyu Hokoku*, No. 30, pp. 27–34, (1986).
"Closer characterization of corona-treated PE surfaces", *Plast. Eng.*, vol. 41, No. 12, pp. 45–48, (1985).
"Chemical characterization of surface-activated polymer films using the ESCA technique", *Physiochem. Aspects Polym. Surf.*, vol. 2, pp. 793–800, (1983).
"Electrical discharge treatment of polypropylene film", *Polymer*, vol. 24, No. 1, pp. 47–52, (1983).
"Corona-discharge treatment of polypropylene films--effects of process parameters: *J. Adhes.*, vol. 11, No. 2, pp. 113–124, (1980).

LOW HYDROHEAD FIBROUS POROUS WEB WITH IMPROVED RETENTIVE WETTABILITY

BACKGROUND OF THE INVENTION

The present invention relates to a method of treating a low hydrohead fibrous porous web material and, for example, to a method that increases the retentive wettability of the web. The invention is also directed to low hydrohead fibrous porous web materials having improved retentive wettability. As used herein the term wettability generally refers to the ability of a material to transmit a fluid through the material. Examples of uses where highly nonwettable materials are desired would be tent and raincoat materials. Conversely, highly wettable materials are desired in, for example, feminine care pad liners and diaper liners. In addition to being wettable, items such as feminine care pad liners and diaper liners are desirably retentively wettable. The term retentively wettable is used herein to designate the degree to which a given material which is wettable retains its ability to be rewet after having been wet and allowed to dry. In other words: how well the material retains it ability to transmit fluids after having already transmitted fluid with intermediate drying.

As is well known, conventional diapers, incontinence garments and feminine care pads have a thin liner that contacts the skin of the wearer and covers the material which absorbs the insulting fluids. These liners are usually made of hydrophobic materials and thus need to be treated with a surface active agent to make them wettable. The liners desirably have low hydrohead values (indicating large pores through the material) because their function is to allow the transmission of fluid with minimal pressure to an adjacent absorbent pad which acts to absorb the fluid. As used herein the term "hydrohead" refers to the ability of a material to support a given column of water under defined conditions. The height of the column of water supported is the hydrohead value. Additionally, the liner should be highly wettable because, as has been previously stated, one of the functions of the liner is to transmit as much fluid to the absorbent material as quickly and completely as possible. Thus, fluid should flow through the liner and into the absorbent before it travels more than a short distance on the surface of the liner. Fluid which fails to flow through the liner is termed "run-off". In some circumstances, run-off may cause undesirable leakage and/or skin irritation problems. Additionally, because feminine care pad liners and, especially, diaper liners continue to be worn after the first of numerous fluid insults, liners used in these items desirably should have a high degree of retentive wettability.

In order to evaluate the retentive wettability characteristics of various liner materials, a stringent run-off test has been developed. While the test is described in detail below, it can generally be stated that the test attempts to approximate or exceed the real-world stresses a porous web material is subjected to when utilized as a diaper liner. This approximation is generally achieved by utilizing 100 milliliters of insulting distilled water test fluid having a surface tension greater than urine and maintaining the porous web material to be tested at a 30 degree incline on top of an absorbent during the insult, i.e. during the run-off test.

In the past, feminine pad liners and diaper liners have been subjected to treatment with surfactants to improve wettability. The liners have been treated with surfactant by (1) passing the formed liner through a bath containing the surfactant in either neat or solution form and drying the liner so that a given amount of the surfactant is deposited on the liner, or (2) spraying a surfactant in either neat or solution form on the fibrous porous web and drying the liner so that a given amount of the surfactant is deposited on the liner, or, (3) adding surfactant to a thermoplastic resin prior to extrusion and formation of the resin into a thermoplastic porous web material. In the later situation, under known process conditions, the added surfactant exudes or migrates to the surface of the fibers of the porous web material during or shortly after fiber formation This phenomenon has been referred to as "blooming" the surfactant. It is believed that blooming results from the insolubility of the surfactant in the thermoplastic polymer as the polymer cools. See U.S. Pat. No. 4,535,020 to Thomas et al (hereafter Thomas et al 020) which demonstrates surfactant blooming in a diaper liner formed from a perforated film.

A liner made from a hydrophobic material, such as a thermoplastic polymer, will not be wet by bodily fluids because the surface tension of the bodily fluid is greater than the critical surface energy of the hydrophobic material Surface tension is the contractile surface force of a fluid where the fluid tries to assume a spherical form and to present the least possible surface area. It is usually measured in dynes per centimeter. Accordingly, because it makes the liner wettable, surfactant is desirably applied to the liner. Application of a surfactant onto a liner material may make a nonwettable liner wettable by at least two mechanisms: (1) Surfactants present on the liner can dissolve into an insulting bodily fluid and lower the surface tension of the resulting solution to more equal the critical surface energy of the liner material. Accordingly, when a surfactant coated liner is insulted with a fluid such as urine, the surfactant acts to lower the surface tension of the fluid and allow the fluid to pass through the liner thus reducing or avoiding unacceptable run-off. In this situation, a certain amount of the surfactant on the liner is lost with each insult and unacceptable run-off occurs at some following insult due to the lack of availability of surfactant to lower the surface tension of the insulting fluid. (2) The surfactant can be coated onto the fibers making up the liner, making the fiber surface of the liner more hydrophilic, i.e., increase the apparent critical surface energy of the fibers. In this situation the liner would be permanently wettable if the surfactant did not dissolve into the insulting fluid.

As any parent will testify, it is an unfortunate event when unacceptable run-off, i.e. non-transfer of urine through the liner and into the absorbent portion of the diaper, occurs. In such a situation leakage of urine from the diaper may occur. A sad aspect of this situation is that, but for the fact that the liner did not allow the urine to pass through to the absorbent material, the diaper may well have had the capacity to absorb the urine. In such a situation the diaper has the capacity to absorb the urine but not the ability.

Accordingly, it has been a goal of those in the art to provide a porous web material which has an improved wettability. This was the initial goal because, if the material is not wettable at all, the material cannot function as a liner in a diaper. It has also been a goal of those in the art to provide a low hydrohead web which will transmit the fluid to a juxtaposed absorbant rather than retain the fluid. Additionally, it has been a goal of those in the art to provide a low hydrohead porous web which has an improved retentive wettability. That is, when dried between insults, the diaper liner has a significant increase in the number of fluid insults that the liner allows to pass through to the absorbent before unacceptable run-off occurs. A desirable goal would be to provide a low hydrohead liner which, prior to unacceptable run-off, would allow fluid to pass through it in multiple, typical-quantity insults in a total quantity at least as great as the absorbing capacity of the absorbent material of the diaper. Thus, the entire absorbing capacity of the diaper could be utilized prior to unacceptable run-off.

Perforated films have been used as diaper liners. See, for example, Thomas et al 020. Corona discharge treatment of films is also old in the art and it is known that corona discharge treatment of a polymer film in the presence of air entails substantial morphological and chemical modifications in the polymer film's surface region. See Catoire et al, "Physicochemical modifications of superficial regions of low-density polyethylene (LDPE) film under corona discharge," *Polymer*, vol. 25, p. 766. et. seq. June, 1984.

Generally speaking, corona treatment has been utilized to either (1) improve the print fastness on the film, or (2) to perforate the film. For example, U.S. Pat. No. 4,283,291 to Lowther describes an apparatus for providing a corona discharge, and U.S. Pat. No. 3,880,966 to Zimmerman et al discloses a method of using a corona discharge to perforate a crystalline elastic polymer film and thus increase its permeability. U.S. Pat. No. 3,471,597 to Schirmer also discloses a method for perforating a film by corona discharge. U.S. Pat. No. 3,754,117 to Walter discloses an apparatus and method for corona discharge treatment for modifying the surface properties of thin layers or fibers which improve the adhesion of subsequently applied inks or paints or of subsequent bonding.

It also is possible to treat a diaper liner material with a corona discharge and then immediately dip the film in a surfactant solution. Because the corona effect on the material generally starts to immediately decay, it is important to get the corona treated material into the bath as quickly as possible. Such a method is discussed in Japanese KOKAI Patent Number SHO63[1988]-211375. This document discloses a method for producing a nonwoven fabric having a long lasting hydrophilicity. The method involves first treating a nonwoven fabric of synthetic fiber by a corona discharge and then coating the treated fabric with about 2-10 grams of surface active agent per square meter of fabric.

Of particular interest is the fact that Thomas et al 020 is directed to the utilization of corona discharge in conjunction with surfactant treated films to effect improved wettability, i.e. higher fluid transmission rates and therefore decreased run-off of fluid. In this regard Thomas et al 020 states that a perforated film which has been treated with surfactant and which is then corona discharge treated results in a film with very low, zero or near zero fluid run-off on the first run-off test. Thomas et al 020 reports that this effect is accomplished because the corona discharge treatment acts on the chemical additive, the surfactant, to provide the perforated film with a zero or near zero percent run off. Thomas et al 020 postulates that this effect is achieved due to the surfactant providing a greater polarizability to the film than the film would have without the surfactant being added. The corona discharge treatment provides additional polarizing effect and, in combination with the surfactant, provides improved wettability. Thomas et al 020 does not appear to address the question of retentive wettability because all of the test results appear to be directed to run-off testing after a single fluid insult.

While of interest to those in the art, the statements made by Thomas et al 020 appear to be of limited value for a number of reasons. Initially, as stated above, Thomas et al 020 appears to be directed toward improved wettability of perforated films as compared to materials having improved retentive wettability materials. Secondly, Thomas et al 020 uses a run-off test procedure which does not, in the opinion of the present inventors, adequately address the environmental stresses a liner is subjected to when it is utilized in a diaper. For example, the Thomas et al 020 run-off test only utilizes 25 milliliter test fluid amounts and not an amount, such as 100 milliliters, which more closely represents the typical amount that is voided by an infant. See, Goeller et al., Urination in the First Three Years of Life, *Nephron*, 28: 174-178 (1981) where it is stated that the mean voiding size of 12-18 month old infants is 57.3+/−21.6 milliliters. It is also stated that the mean voiding size of 24-32 month old infants is 79.3+/−14.9 milliliters. Thirdly, Thomas et al 020 uses a run-off test solution which is stated to contain 0.025 percent of alkylaryl polyether alcohol bearing the trade name "Triton X-100" and manufactured by the Rohm & Haas Company. Triton X-100 is, itself, a surface tension reducing agent. Rohm & Haas literature states that 0.01% of X-100 added to water reduces the surface tension of the solution to 31 dynes/cm at 25 degrees C. Clearly the 0.025 percent of X-100 present in the test solution of Thomas et al 020 should have an effect on the wettability of the perforated film, regardless of the type of treatment to which the perforated film is subjected. By comparison, the run-off test procedure used herein is more demanding because it utilizes distilled water as the test solution. Because the distilled water which was used had a surface tension of about 60 dynes per centimeter, it has a higher surface tension that the surface tension of infant urine which, while it varies somewhat with age, is approximately 55 dynes/centimeter. Lastly, the incline at which the liner material to be tested is placed is merely 10 degrees in the Thomas 020 run-off test as compared to the 30 degree incline of our test.

To demonstrate the effect of adding Triton X-100 to the test solution on wettability, run-off testing, as defined below, was conducted on conventional (non-surfactant treated) 0.8 ounce per square yard porous polypropylene web spunbonded material. In these tests, the test fluid was maintained at 37+/−1 degrees Centigrade. Three samples were run using distilled water as the test fluid and three samples were run where the test solution was 99.9751% distilled water and 0.0249% Triton X-100. Additionally, each of these tests was duplicated with the exception that (1) the incline was reduced to 10 degrees; (2) the quantity of test solution was reduced to twenty-five (25) grams and (3) the test fluid was maintained at room temperature. These modifications were made to approximate the test procedure stated in Thomas et al 020. Using our run-off procedure, the average run-off of the 100 grams distilled water only samples was 90.6+/−0.7 grams (90.6% run-off). Clearly an unacceptable amount of run-off. Compared to this, the average run-off of the distilled water with 0.0249% Triton X-100 was 3.7+/−1.8 grams (3.7% run-off). The effect of the presence of the Triton X-100 is clear. Without any surfactant modification of the test fibrous porous web, the fibrous porous web now has apparently acceptable run-off. If the approximation of the Thomas et al 020 test is utilized, the average run-off of the 25 gram distilled water only sample is 21.5+/−0.7 grams (86% run-off). Lastly, if a 99.9751% distilled water and 0.0249% Triton X-100 fluid is used on the 10 degree incline, the average run-off value is 1.6+/−2.2 grams (6.4%) run-off. Once again, the effect of the presence of the Triton-X100 is clear.

Surface tension measurements of both fluids were made after the measuring equipment had been checked for accuracy against a very pure sample of distilled water. The sample of very pure distilled water gave a value of 71.8 dynes/centimeter, reflecting correct calibration and procedure. The average of three surface tension measurements of the laboratory distilled water used was 59.13 dynes/centimeter reflecting the presence of slight impurities in the laboratory distilled water. After addition of the Triton X-100 to the laboratory distilled water, the average of three surface tension measurements for this fluid was 30.7 dynes/centimeter. This correlates well with our run-off testing of the two fluids. From these data it is clear that the presence of the Triton X-100 in the test fluid affects the run-off test results to make the material appear more wettable.

In summary, the Thomas et al 020 test results tend to identify those materials which somewhat enhance the wettability of a liner material. In other words, those materials whose use results in an improvement for a given, single insult with the insult being of limited quantity. However, Thomas et al 020 appears to fail in identifying the materials which result in improved retentive wettability. Said yet another way, Thomas et al 020 fails to identify those surface active agents whose utilization results in an increase in the number of run-off tests a given material can be subjected to without unacceptable run-off occurring. Accordingly, it can be seen that there still exists a need for a fibrous porous web material having improved retentive wettability so that the web can be used as, for example, a diaper liner. Such a web material desirably would have reduced fluid run-off when multiple insults of at least about 100 milliliter are applied. It is such a material to which our invention is directed. Specifically, our invention is directed toward substances which, in combination with corona discharge treatment, increase the retentive wettability of fibrous porous web materials by increasing the number of run-offs tests the material can be subjected to by at least 50%, without the occurrence of unacceptable run-off. In many instances the number of run-offs prior to unacceptable run-off is increased by at least 100%. In some instances the number of run-offs prior to unacceptable run-off is increased by at least 200%.

SUMMARY OF THE INVENTION

In response to the aforementioned shortcomings and difficulties in the prior art, we have devised a method of treating a low hydrohead fibrous porous web material to increase the web's retentive wettability, by at least about 50%, as compared to untreated web material. The increase in retentive wettability is demonstrated by an increase in the average number of run-off tests that the treated low hydrohead web material can sustain without unacceptable run-off. The method includes the steps of (1) adhering to the low hydrohead fibrous porous web material at least about 0.05%, by weight of the web material, of a surface active agent having a hydrophile-lipophile balance of at least about 6; and (2) applying a corona discharge equivalent to a charge of at least about 0.6 watt minute per square foot per side of the web material to the surface active agent bearing web material.

From about 0.05% to about 3%, by weight of the web material, of surface active agent may be adhered to the web material. For example, from about 0.1% to about 1%, by weight of the web material, of surface active agent may be adhered to the web material. More particularly, from about 0.1% to about 0.4%, by weight of the web material, of surface active agent may be adhered to the low hydrohead web material. Even more particularly, from about 0.2% to about 0.3%, by weight of the web material, of surface active agent may be adhered to the web material.

The equivalent of from about 0.6 to about 10 watt minute per square foot per side of the low hydrohead web material of corona discharge may be applied to the web material. For example, the equivalent of from about 1 to about 5 watt minute per square foot per side of the web material of corona discharge is applied to the web material. More particularly, the equivalent of from about 2 to about 4 watt minute per square foot per side of the web material of corona discharge is applied to the web material.

In one embodiment our process is directed to the modification of the process for forming a low hydrohead thermoplastic fibrous porous web material to increase, by at least about 50%, as compared to unmodified web material, the number of run-off tests that the web material can sustain without unacceptable run-off. The method includes the steps of (1) forming a melt from a thermoplastic fiber forming material; (2) adding, to the melt, an amount of surface active agent having a hydrophile-lipophile balance of at least about 6 sufficient to effect a surface concentration of the surface active agent of at least about 0.05%, by weight of the resulting fibrous porous web material; (3) forming the melt into fibers and the fibers into a fibrous porous web under conditions which allow at least 0.05%, by weight of the fibrous porous web, of the surface active agent to bloom to the surface of the fibers of the porous web; and (4) applying a corona discharge equivalent to a charge of at least about 0.6 watt minute per square foot per side of the porous web to the surface active agent bearing web material.

Because not all of the surface active agent added to the melt blooms, the amount of surface active agent added to the melt is generally greater than the amount desired to be present on the surface. Accordingly, the amount of surface active agent added to the melt may vary with the surface active agent used, the thermoplastic material used to form the web and/or the process conditions of forming the web.

As is the case generally, in this embodiment the equivalent of from about 0.6 to about 10 watt minute per square foot per side of the web material of corona discharge may be applied to the web material. For example, the equivalent of from about 1 to about 5 watt minute per square foot of the web material of corona discharge is applied to the web material. More particularly, the equivalent of from about 2 to about 4 watt minute per square foot of the web material of corona discharge is applied to the web material.

In some embodiments the number of run-off tests prior to unacceptable run-off may be increased by at least about 100%. In other embodiments, the number of run-off tests prior to unacceptable run-off may be increased by at least about 200%.

In all embodiments the surface active agent may be selected from the group including one or more surfactants, emulsions and dispersants.

In all embodiments the hydrophile-lipophile balance of the surface active agent will be about 6 or greater. For example the hydrophile-lipophile balance may range from 6 to about 20. More particularly, the hydrophile-lipophile balance of the surface active agent may range from 8 to about 20. Even more particularly, the hydrophile-lipophile balance of the surface active agent may range from 10 to about 20.

As is stated below, the low hydrohead porous web material generally has a hydrohead of less than about 25 centimeters of water. For example the hydrohead of the porous web material may be less than about 20 centimeters of water. In one embodiment, the hydrohead of the low hydrohead porous web material may be about 15 centimeters of water.

The present invention is also directed to products prepared by or preparable by our process. That is, the invention is generally directed to a fibrous porous web material having improved retentive wettability of at least about 50%. The web material includes (a) a low hydrohead fibrous porous web; and (b) a surface active agent having a hydrophile-lipophile balance of six (6) or greater adhered to the low hydrohead fibrous porous web material. At least about 0.05%, by weight of the web material of surface active agent is adhered to the web material. Additionally, a corona discharge equivalent to a charge of at least about 0.6 watt minute per square foot per side of the web material has been applied to the surface active agent bearing low hydrohead web material.

The fibrous porous web material may include a polyolefin or a blend of polyolefins or any other suitable material which may be formed into a low hydrohead fibrous porous web. For example, the fibrous porous web may be formed from polyethylene or polypropylene.

The fibrous porous web material may be formed by any of the wide variety of processes which provide a low hydrohead fibrous porous web. For example, the fibrous porous web may be formed by spunbonding so that the fibrous porous web includes spunbonded fibers or from meltblowing processes designed to produce larger macrofibers.

OBJECTS OF THE INVENTION

Accordingly, it is a general object of the present invention to provide a method whereby the retentive wettability of a low hydrohead fibrous porous web material is increased by at least about 50%.

Another general object of the present invention is to provide a low hydrohead fibrous porous web material having an increased retentive wettability of at least about 50%.

Still further objects and the broad scope of applicability of the present invention will become apparent to those of skill in the art from the details given hereinafter. However, it should be understood that the detailed description of the presently preferred embodiments of the present invention is given only by way of illustration because various changes and modifications well within the spirit and scope of the invention will become apparent to those of skill in the art in view of the following description.

DEFINITIONS AND TESTS

Figure 1:
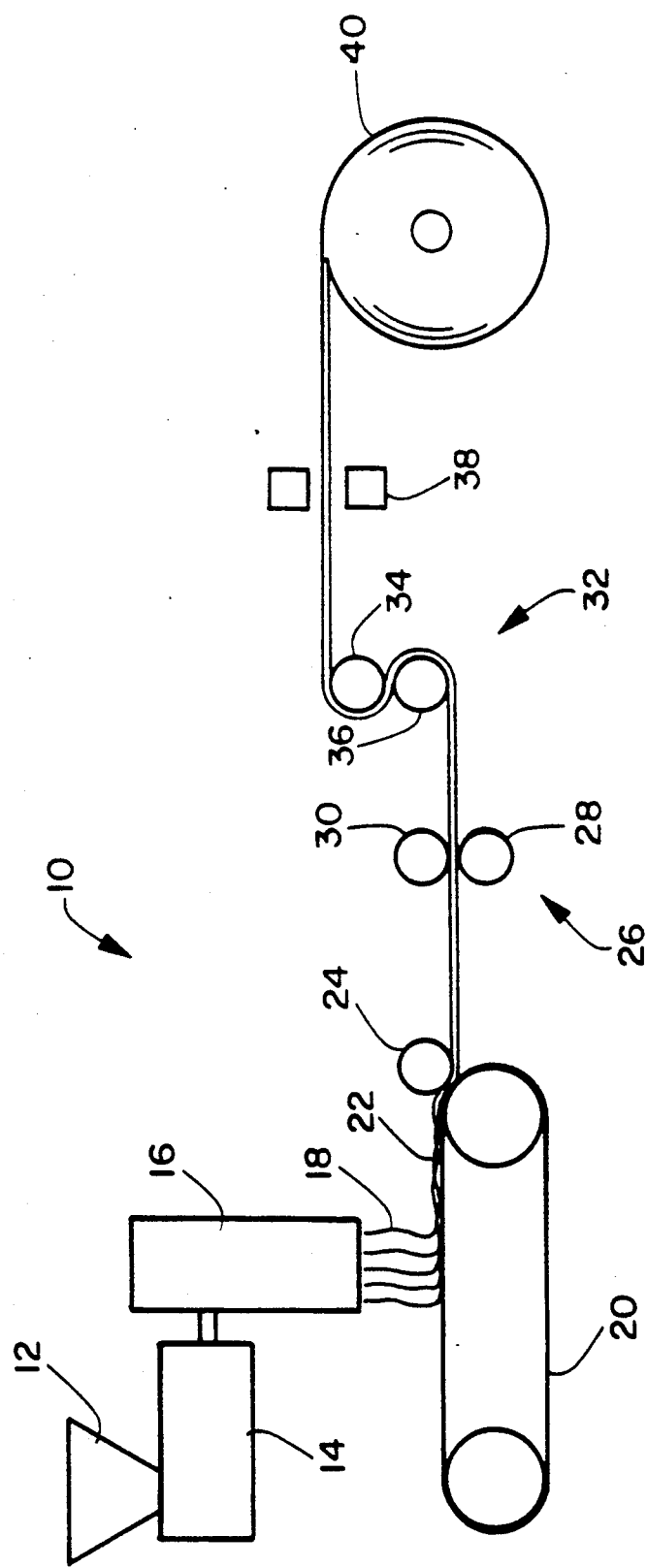
FIG. 1 is a schematic representation of one process for carrying out the present invention.

Unless otherwise specifically so stated, all run-off data reported herein were obtained using the following run-off test. Once a fibrous porous web material is selected for testing, a sheet of the material measuring sixteen (16) inches long, in the machine direction, and fifteen (15) inches wide is laid, without applied pressure, against the absorbent of a Huggies trademarked brand diaper, large size. The diaper has had its inner body side liner removed and any elastic leg and elastic waist material removed so that the absorbent will assume a generally flat configuration. The polyethylene film backing and tissue top cover are left on the absorbent to give it structure so that it can be handled. Prior to placement of the test material on top of the absorbent, the absorbent is placed, film side down, on a water impervious plane inclined at 30 degrees to horizontal and terminating, at its lower edge, with a V-shaped raised edge which directs any fluid impacting the raised edge toward a hole in the plane which is centrally located at the vertex of the V. A 250 milliliter beaker is located beneath the hole to collect any fluid passing therethrough. The absorbent is positioned on the inclined plane so that the top of the front panel constitutes its lower free edge on the inclined plane. The lower free edge is located approximately 300 millimeters from the point of impact of testing fluid. A funnel arrangement with a stopcock is positioned above the diaper approximately 300 millimeters from the lower free edge of the absorbent and in such manner that an approximate 32 millimeter clearance exists between the top of the absorbent and the lower tip of the funnel. The lower free edge of the absorbent is located approximately 150 millimeters up the incline from the hole in the inclined plane. The test material is positioned over the absorbent so that it overhangs the fluff of the diaper by about 25 millimeters. Approximately one hundred milliliters of distilled water maintained at 37 degrees C. +/−0.6 degrees C. is poured into the funnel with the stopcock closed. The funnel stopcock is opened to allow the test fluid to flow from the funnel onto the test material at a rate so that all 100 milliliters is dispensed in about eighteen seconds. Fluid which is collected within the 250 milliliter beaker is "run-off". The amount of run-off for a given test is measured in grams. The test material is removed from contact with the underlying absorbent, hung vertically and permitted to air dry at room temperature. Typically, about 15 minutes are necessary to dry the test material. The test material is then laid against a new, equivalent absorbent prepared as stated above, and the procedure is repeated as described above with the test material being placed so that the distilled water initially impacts the test material at the point of impact of the previous test(s). Because of test material wrinkling and the irregular surface of the underlying absorbent material, the path taken by the distilled water in subsequent runs may differ from its path taken in prior runs and affect results. Additionally, some test fluid may get hung up on the test apparatus.

As used herein the term "unacceptable run-off" relates to the testing of a material by the above-identified run-off test and the test resulting in run-off of ten (10) grams of test fluid or more.

As used herein the term "high hydrophile-lipophile balance" refers to a surface active agent having a hydrophile-lipophile balance of about six (6) or greater.

As used herein the term "surface active agent" refers to any compound that reduces surface tension when dissolved in water or water solutions or which reduces interfacial tension between two liquids, or between a liquid and a solid. There are three general categories of surface active agents: detergents, wetting agents (i.e. surfactants) and emulsifiers.

The term "hydrophile-lipophile balance" (HLB) is well known to those in the art. The HLB of a nonionic surfactant is the approximate weight percent of ethylene oxide in the surfactant divided by 5. The numerical scale of HLB values ranges from 1 (completely lipophilic or oil-loving) to 20 (completely hydrophilic or water-loving). Refer to W. C Griffin, *J. Soc. Cosmetic Chemists* 317-326 (1949). In some instances the HLB of a material is determined by comparing its activity to known materials having known HLB's to get an equivalent HLB. Equivalent HLBs can sometimes exceed 20.

As used herein the term "low hydrohead material" refers to a porous web material which supports no more than 25 centimeters of water when its hydrohead is measured in accordance with Method 5514 - Federal Test Methods Standard No. 191A. In all cases the hydrohead of the porous web material is measured prior to treatment with surface active agent and corona discharge as is required by the present invention.

DETAILED DESCRIPTION OF THE PREFERRED EMBODIMENT

Referring now to the drawings where like reference numerals represent like structure or like process steps and, in particular, to FIG. 1 which schematically illustrates apparatus 10 for forming and treating a low hydrohead fibrous porous web material to improve the retentive wettability of the low hydrohead material so that the treated web material can survive an average of at least 50% more run-off tests without experiencing unacceptable run-off. The process may be initiated by blending pellets (not shown) of a fiber-forming thermoplastic material which may be, for example a polyolefin or a blend of polyolefins such as polypropylene or polyethylene, and a bloomable surface active agent having a hydrophile-lipophile balance of at least about 6 into the hopper 12 of an extruder 14.

While any thermoplastic fiber forming material may be useful, one desirable material is a polypropylene which may be obtained from the Shell Chemical Company under the trade designation 5A09. The Shell 5A09 polypropylene has a melt flow rate of about 40 decigrams per minute when measured in accordance with ASTM D 1238 at 230 degrees Centigrade.

Many other thermoplastic polymers are suitable for use as the fiber forming polymer. Specific, non-limiting examples of such polymers include: polyolefins such as low density polyethylene, linear low density polyethylene, high density polyethylene and ethylene/propylene copolymers. The materials may be plasticized with suitable plasticizers, and other additives known in the art may be added to achieve the desired physical characteristics.

Elastomeric polymers may be used to form the fibrous porous web. Such polymers include: polyester elastomeric materials, polyurethane elastomeric materials, polyetherester elastomeric materials, polyamide elastomeric materials, and the various elastomeric A-B-A' block copolymer materials disclosed in U.S. Pat. No. 4,663,220 to Wisneski et al, which is hereby incorporated by reference.

The bloomable surface active agent may be, for example, an emulsion, a wetting agent such as a surfactant, or a detergent having a hydrophile-lipophile balance of at least about 6 or greater which is bloomable. The bloomable surface active agent may be nonionic, cationic or anionic. If the bloomable surface active agent is nonionic, it is desirable that it have at least 3 ethylene oxide groups. One desirable bloomable surface active agent is a surfactant which may be obtained from the Rohm & Haas Company under the trade designation Triton X-102. Rohm & Haas literature states that the X-102 is a nonionic octylphenol liquid surfactant having from 12-13 ethylene oxide units. The material is about 73%, by weight, ethylene oxide, has a Brookfield viscosity at 25 degrees C. (12 rpm) of 330, and has a calculated hydrophile-lipophile balance of about 14.6. Other Triton brand name materials may be utilized in the present invention. Exemplary of which are Triton X-35 which is a nonionic octylphenol series material having three ethylene oxide units and a calculated hydrophile-lipophile balance of 7.8; Triton RW 50 which is a cationic material, (t-$C_{12-14}$NH($CH_2CH_2O)_5$H), having an average of five ethylene oxide units and a measured hydrophile-lipophile balance of 12-14; Triton RW 100 which is a cationic material, (t-$C_{12-14}$NH($CH_2CH_2O)_{10}$H, having an average of 10 ethylene oxide units and a measured hydrophile-lipophile balance of 16; Triton DF 12 which is a nonionic modified polyethoxylated alcohol that has a calculated hydrophile-lipophile balance of 10.6 and Triton DF 18 which is a nonionic biodegradable modified alcohol that has a calculated hydrophile-lipophile balance of 11.3.

It is desirable for the surface concentration of the surface active agent on the surface of the fibers of the low hydrohead web to be at least about 0.05 weight percent of the web. For example, from about 0.05 percent, by weight, to about 3 percent, by weight of the web. More particularly, from about 0.10 percent, by weight, to about 1.0 percent, by weight of the web. For example, from about 0.1 percent, by weight, to about 0.4 percent, by weight, of the web. Even more particularly, from about 0.20 percent, by weight, to about 0.30 percent by weight of the web. In one embodiment the surface concentration is about 0.26 percent by weight of the low hydrohead web 22.

Because not all of the surface active agent added to the melt blooms, the amount of surface active agent added to the melt is generally greater than the amount desired to be present on the surface. Accordingly, the amount of surface active agent added to the melt may vary with the surface active agent used, the thermoplastic material used to form the web and/or the process conditions of forming the web.

If Triton X-102 is used as the surface active agent and polypropylene is the thermoplastic material, the blend will contain at least about 0.45 percent, by weight, of the high hydrophile-lipophile balance surface active agent. For example, the blend may include from about 96.6 percent, by weight, to about 99.55 percent, by weight, of the fiber forming polymer and from about 0.45 percent, by weight, to about 3.4 percent, by weight, of the high hydrophile-lipophile balance surface active agent. Desirably, the blend includes from about 98.6 percent, by weight, to about 99.5 percent, by weight, of the fiber forming polymer and from about 0.5 percent, by weight, to about 1.4 percent, by weight, of the high hydrophile-lipophile balance surface active agent. For example, the blend may include from about 99.2 percent, by weight, to about 99.5 percent, by weight, of the fiber forming polymer and from about 0.5 percent, by weight, to about 0.8 percent, by weight, of the high hydrophile-lipophile balance surface active agent. In one embodiment the blend may include from about 99.3 percent, by weight, to about 99.4 percent, by weight, of the fiber forming polymer and from about 0.6 percent, by weight, to about 0.7 percent, by weight, of the surface active agent.

The temperature of the blend is elevated within the extruder 14 by a conventional heating arrangement (not shown) to melt the blend and pressure is applied to the blend by the pressure-applying action of a turning screw (not shown), located within the extruder, to form the blend into an extrudable composition. Desirably the blend is heated to a temperature of at least about 175 degrees Centigrade if polypropylene is utilized as the fiber forming polymer in the blend. The blend is then forwarded by the pressure applying action of the turning screw to a fiber forming arrangement 16 which may, for example, be a conventional spunbonding die arrangement. The hydrohead of conventional spunbonded material of diaper liner weight has been measured to be about 15 centimeters of water. Spunbonding fiber forming arrangements are described in U.S. Pat. Nos. 4,340,563 to Appel et al and 4,405,297 to Appel et al. Both of these patents are hereby incorporated by reference. The elevated temperature of the blend is maintained in the fiber forming arrangement 16 by a conventional heating arrangement (not shown). The fiber-forming arrangement generally extends a distance in the cross-machine direction which may be about equal to the width of the fibrous porous nonwoven web which is to be formed by the process. The fiber-forming arrangement 16 extrudes and attenuates the fibers 18 and directs them onto a moving forming screen 20. Upon impacting the forming screen 20, the fibers 18 may, depending upon known process conditions, adhere to each other to form the low hydrohead fibrous porous web 22. If not, a nip roller 24, in combination with the forming screen 20 can act to make the web 22 self supporting. If desired, the low hydrohead web 22 may be passed through a thermal point bonding arrangement 26 including rollers 28 and 30 to consolidate the web 22 even further. If the fibrous porous web 22 is to be used as a diaper liner, the basis weight of the web is desirably 35 grams per square meter (g/m$^2$) or less, for example, in the range of 10 through 30 g/m$^2$. The combination of elevated temperature and elevated pressure conditions which effect extrusion of the blend will vary over wide ranges. For example, at higher elevated temperatures, lower elevated pressures will result in satisfactory extrusion rates and, at higher elevated pressures of extrusion, lower elevated temperatures will effect satisfactory extrusion rates.

After formation of the low hydrohead fibrous porous web 22, the high hydrophile-lipophile surface active agent is bloomed to the surface of the web 22. In many instances the heat of the molten fibers 18 cooling after extrusion will be sufficient to effect blooming of the high hydrophile-lipophile balance surface active agent. However, in some instances, the web 22 will have to be passed through a heating arrangement 32 which can include heating cans 34 and 36 to effect blooming. The heating can blooming temperature will vary with the surface active agent and polymer utilized. However typical temperatures for polypropylene and Triton X-102 range from 250 degrees F. to 300 degrees F. For example, from about 265 degrees F. to about 275 degrees F. Residence time of the web 22 on the heating cans 34 and 36 will vary with line speed. Typical residence times are in the range of 2-7 seconds. In any event the blooming conditions are to be adjusted so that at least about 0.05, weight percent of the resultant web 22, will bloom to the surface of the web 22. For example, from about 0.05 percent, by weight, to about 3 percent, by weight of the web 22 of surface active agent will bloom to the surface of the web 22. More particularly, from about 0.10 percent, by weight, to about 1.0 percent, by weight of the web 22, of surface active agent will bloom to the surface of the web 22. For example, from about 0.1 percent, by weight, to about 0.4 percent, by weight, of the web 22, of surface active agent will bloom to the surface of the web 22. Even more particularly, from about 0.20 percent, by weight, to about 0.30 percent by weight of the web 22, of surface active agent will bloom to the surface of the web 22.

Determination of the weight percentage of the surface active agent on the surface of the low hydrohead web at this point in the process can be determined by: (1) weighing the initial sample of material; (2) quantitatively extracting the surface active agent from the surface of the web 22 using an appropriate solvent; (3) determining the amount of surface active agent in the extraction solvent by such means as ultraviolet spectroscopy, infra-red spectroscopy, gravimetric analysis etc. (This may require making up a series of concentration standards of the surface active agent in the extracting fluid to calibrate the analytical equipment/method/technique. Manufactrues of surface active agent often will supply methods for determining surface active agent quantitatively and qualitatively.); and (4) dividing the amount of surface active agent by the initial web 22 sample weight and multiplying by 100.

Once the high hydrophile-lipophile balance surface active agent has been bloomed to the surface of the web 22, the web 22 is passed through the gaps of two conventional corona discharge units 38. The two corona units are arranged so one treats one side of the web 22 and the other treates the other side of the web 22. One desirable corona discharge unit can be obtained from Enercon Ind. Corporation under trade designation Model SS 1223. The gaps of the corona discharge treatment apparatus may be maintained at about 0.065 inches. Standard metal rolls are used as the groung electrode. The base metal groung electrode roll may be buffered with 1 wrap of 0.5 mil polyester to substantially prevent arcing of the corona unit and pinholing in the fibrous porous web 22. Such buffering reduces the effectiveness of the corona discharge unit by approximately 20% for each wrap of 0.5 mil film used. The line speed of the web material 22 and the voltage and amperage of the corona discharge unit 38 are adjusted so that the equivalent of at least about 0.6 watt minute per square foot per side of corona discharge is applied to the web material 22. For example, the equivalent of from about 0.6 to about 8 watt minute per square foot per side of the web material 22 of corona discharge may be applied to the web material 22. Accordingly, the equivalent of from about 1 to about 5 watt minute per square foot per side of the web material 22 of corona discharge may be applied to the web material 22. More particularly, the equivalent of from about 2 to about 3 watt minute per square foot per side of the web material 22 of corona discharge may be applied to the web material 22.

Once the corona discharge unit 38 has applied the appropriate amount of charge to the web material 22, the web material 22, may be wound up on a storage roll 40. The web material 22 may later be used in a wide variety of applications which require or desire utilization of a material having acceptable retentive wettability. This method of treating a fibrous porous web material 22 has been found to increase, by at least about 50%, as compared to non-corona treated web material, the number of wettings (i.e. run-off tests that can be passed) that the web material 22 can sustain without unacceptable run-off.

Figure 2:
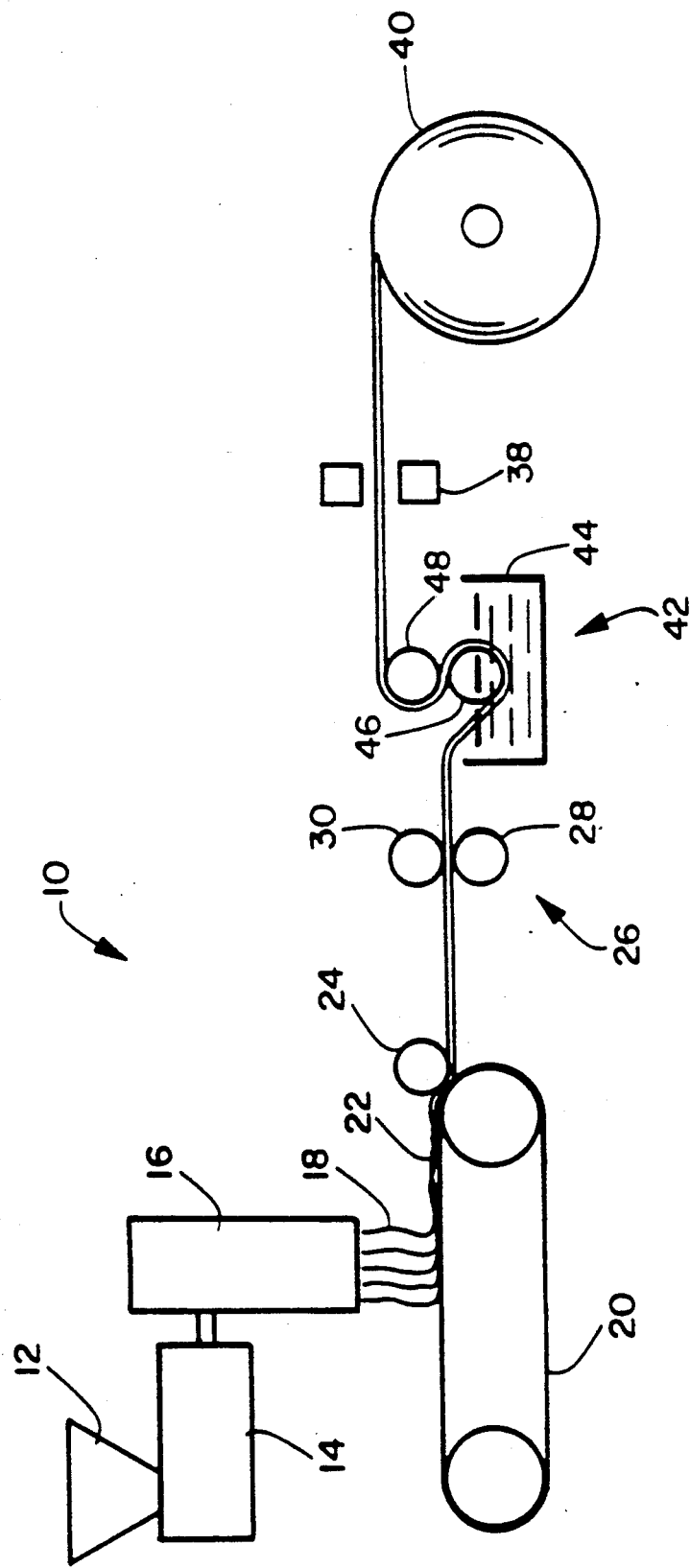
FIG. 2 is a schematic representation of a second process for carrying out the present invention.

In another embodiment, schematically illustrated in FIG. 2, a nonblooming process is used. In this situation the surface active agent may be applied in neat form or from solution by any of a number of conventional application methods. Exemplary of which are spraying and dip-and-squeeze. The dip-and-squeeze method is illustrated in FIG. 2 with the dip-and-squeeze apparatus 42 including a dipping bath 44 and a pair of squeezing rollers 46 and 48. In this process at least about 0.05%, by weight, of the web material 22 of high hydrophile-lipophile balance surface active agent is applied to the web material 22. For example, from about 0.05% to about 3%, by weight of the web material, of high hydrophile-lipophile balance surface active agent may be applied to the web material 22. Even more particularly, from about 0.1% to about 1%, by weight of the web material 22, of high hydrophile-lipophile balance surface active agent may be applied to the web material 22. More particularly, from about 0.1% to about 0.4%, by weight of the web material 22, of high hydrophile-lipophile balance surface active agent may be applied to the web material 22. Even more particularly, from about 0.2% to about 0.3%, by weight of the web material 22, of high hydrophile-lipophile surface active agent may be applied to the web material 22.

By varying the amount of high hydrophile-lipophile balance surface active agent present of the surface of the web material 22 and the amount of corona discharge applied to the web 22, the number of run-off tests to which the treated web 22 can be subjected prior to unacceptable run-off may be increased by at least about 50%. For example, the number of wettings prior to unacceptable run-off may be increased by at least about 100%. In some instances, the number of wettings prior to unacceptable run-off may be increased by about 200%.

Of course, other conventional methods can be used for the production of the nonwoven web 22.

EXAMPLE I

In order to demonstrate the improved retentive wettability of corona discharge treated high hydrophile-lipophile balance surface active agent coated low hydrohead web materials, a low hydrohead spunbonded polypropylene was treated with a variety of of surface active agents in accordance with the present invention. Run-off testing of these materials was conducted to provide evidence of the improved retentive wettability.

Test samples were prepared by first determining about how many grams of a surfactant-containing solution the web to be evaluated would hold. Knowing this value (in grams of solution per gram of web) and the amount of surfactant (in weight percent) desired on the web, a surfactant-containing solution was made. Either an alcohol based or water based surfactant solution was used depending on the surfactant's water solubility. The concentration in the solution was the desired concentration of the surfactant on the web divided by the grams of surfactant the web would hold per gram of web. For example, if the web held 5 grams of solution per gram of web and a 0.3% add on was desired, a 0.06% solution was used.

Once a solution of a chosen surface active agent was made, six (6) 16 inch by 15 inch samples of conventional, low hydrohead, spunbonded polypropylene web material having a basis weight of about 27 grams/square meter, were dipped into the solution and held horizontal while being dried. The hydrohead of such spunbonded polypropylene material before being surface active agent coated/treated is generally about 15 centimeters of water. The goal was to apply 0.3 percent, by weight of the spunbonded web, of surface active agent to each web. In other words, about 0.08 grams per square meter of web.

Next, three of the samples of surfactant coated low hydrohead web material were subjected to 8.3 watt minute per square foot per side of corona discharge treatment so that, for each surface active agent selected, three (3) samples that were only surfactant treated existed and three (3) samples that were surfactant treated followed by corona discharge treatment existed. It should be noted that the grounded electrode roll of each of the two three foot long electrode arrangements used was a metallic roll and was shielded with 1 wrap of 0.5 mil thickness mylar to prevent short circuiting the corona discharge. It is known that this action lowers the effective corona discharge on the spunbonded web by about 20 percent or to about 6.6 watt minute per square foot. The samples were allowed to age for at least three days to ensure that no residual effect of the corona discharge alone would be measured.

Each of the six samples for each of the selected surface active agents was then subjected to the run-off test which is defined above. As has been stated previously, failure was defined as the first run-off test in which a sample evidenced ten or more grams of run-off. In many cases additional run-off testing was conducted to see how consistent the failure point was. That is, having once failed, would the web continue to fail. This was certainly not the case. In spite of this fact, it was decided that the most rigorous and practical definition of failure was one which used the first failing run-off test as the failure point. After the run-off testing was conducted, the values for each of the three samples that were only surface active agent (SAA) treated were averaged and rounded to the nearest whole number and the values for each of the three samples that were both surface active agent treated and corona discharge treated were averaged and rounded to the nearest whole number. These data are reported in Table I.

TABLE I

| Material[1] | HLB | Run-offs, SAA only | Run-offs SAA & Corona | Run-offs, % Improvement |
|---|---|---|---|---|
| SPAN 85[2] | 1.8 | 1 | 1 | 0 |
| ATMUL 84[3] | 2.8 | 2 | 1 | 0 |
| Triton X-15[4] | 3.6 | 1 | 1 | 0 |
| ATLAS G946[5] | 4.3 | 7 | 7 | 0 |
| ARACEL 40[6] | 6.7 | 3 | 20 | 567 |
| Triton X-35[7] | 7.8 | 2 | 15 | 650 |
| ARACEL 20[8] | 8.6 | 9 | 14 | 56 |
| TRITON DF 12[9] | 10.6 | 9 | 16 | 78 |
| ARACEL 165[10] | 11 | 1 | 4 | 300 |
| TRITON DF 18[11] | 11.3 | 11 | 23 | 109 |
| TRITON X 102[12] | 14.6 | 9 | 24 | 167 |
| TRITON RW 50[13] | 13 | 5 | 12 | 140 |
| TRITON RW 100[14] | 16 | 5 | 10 | 100 |

[1]All materials used alcohol solutions except Triton DF 18, Triton X-102, Triton RW 50 and Triton RW 100 which used water solutions.
[2]Sorbitan trioleate obtained from ICI Americas Inc.
[3]Mono and diglycerides from the glyerolysis of edible fats, obtained from Kraft Industries, Memphis Tenn.
[4]Octylphenoxypoylethoxyethanol having one ethylene oxide group, obtained from the Rohm and Haas Co.
[5]Nonionic surfactant, obtained from ICI Americas Inc.
[6]Sorbitan monopalmitate, obtained from ICI Americas Inc.
[7]Octylphenoxypolyethoxyethanol having three ethylene oxide groups, obtained from the Rohm and Haas Co.
[8]Sorbitan monolaurate, obtained from ICI Americas Inc.
[9]modified polyethoxylated alcohol, obtained from the Rohm and Haas Co.
[10]50% polyoxyethylene stearic acid/50% mono and diglycerides of fatty acids, obtained from ICI Americas Inc.
[11]90% Biodegradable modified alcohol/10% water, obtained from Rohm and Haas Co.
[12]Octylphenoxypoylethoxyethanol having 12-13 ethylene oxide groups, obtained from the Rohm and Haas Co.
[13]99.5% t-polyethoxy amine/0.5% t-alkyl primary amine, obtained from the Rohm and Haas Co.
[14]99.5% t-polyethoxy amine/0.5% t-alkyl primary amine, obtained from the Rohm and Haas Co.

From the above data it is clear that a significant increase in retentive wettability of the low hydrohead web material is achieved if the hydrophile-lipophile balance of the surface active agent is greater than 6.

Figure 3:
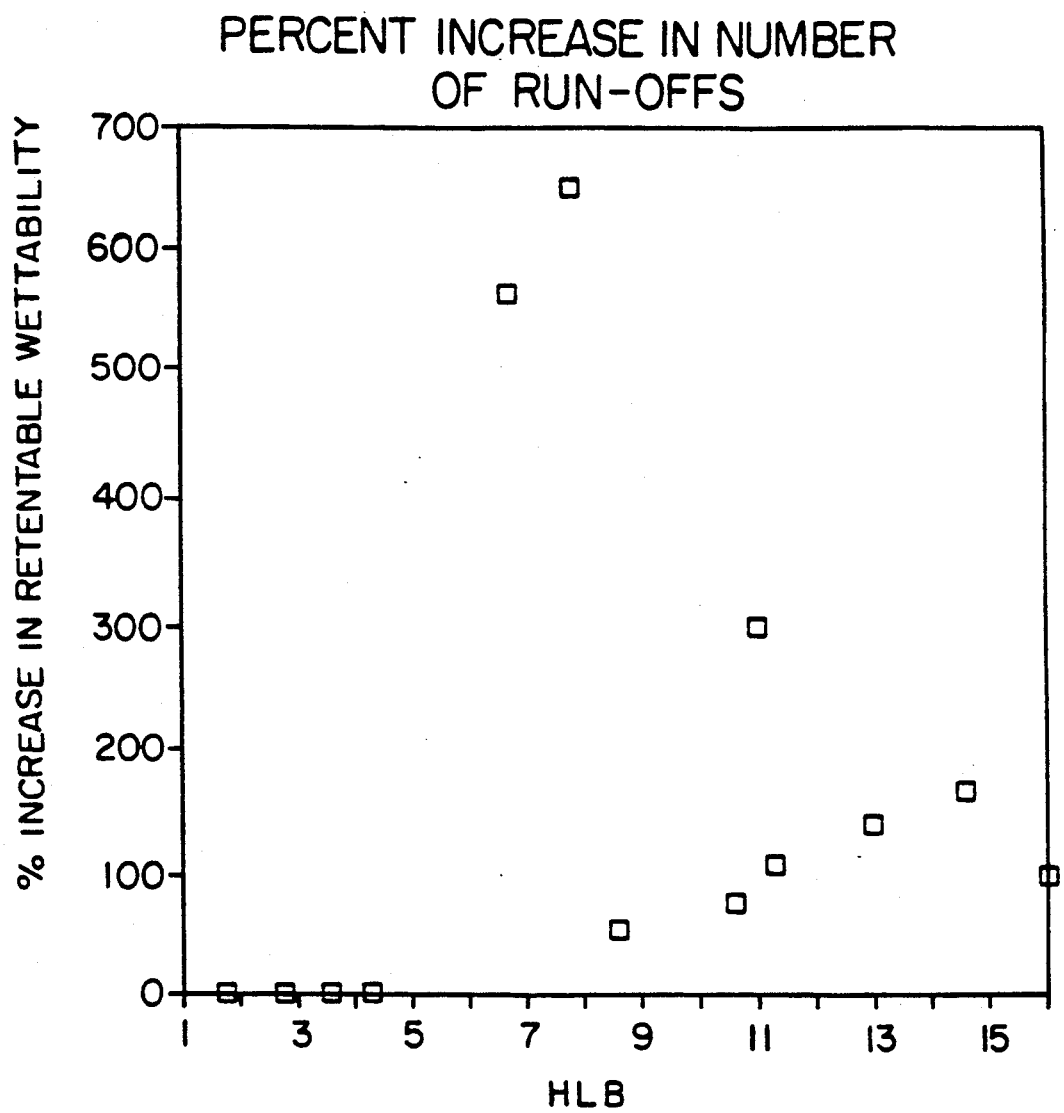
FIG. 3 is a graph illustrating the relationship between hydrophile-lipophile balance and the improvement in retentive wettability of fibrous porous web materials formed in accordance with the present invention as evidenced by the percentage improvement in the number of run-off tests to which a fibrous porous web can be subjected without unacceptable run-off occurring.

These results are graphically presented in FIG. 3. From the above results, it is clear that, once the hydrophile-lipophile balance of the treating material exceeds about 6, significantly improved longevity in the run-off test results after corona treatment are achieved. Of note is that the run-off test employed, in the opinion of the inventors, more accurately approximates a real world situation than the test employed by Thomas et al because 100 milliliters of test fluid is used. This amount is believed to much more accurately approximate the amount voided by an infant. The test is more rigorous also in that a 30 degree, as opposed to a 10 degree, incline is utilized.

EXAMPLE II

To investigate the relationship on the increase in retentive wettability and the percentage of surface active agent applied to the low hydrohead fibrous porous web, eighteen samples of conventional spunbonded material were obtained as above. Solutions of Triton X-102 and Triton DF-18 were prepared. The procedure outlined above was followed with the exception that the target applied amount of surface active agent was reduced to 0.1%, by weight of the fibrous porous web. Additionally, nine samples for each agent were prepared with three samples being surface active agent treated only and six samples being both surface active agent treated and corona treated, as in Example 1, with 6.6 watt minute per square foot of web.

The results of this testing are recorded in Table II.

TABLE II

| Material | HLB | Run-offs, SAA only | Run-offs SAA & Corona | Run-offs, % Improvement |
|---|---|---|---|---|
| TRITON DF 18[15] | 11.3 | 7 | 18—[16] | 157+ |
| TRITON X 102[17] | 14.6 | 3 | 12[18] | 300 |

[15]90% Biodegradable modified alcohol/10% water, obtained from Rohm and Haas Co.
[16]Average of six runs rounded off to the nearest whole number. Two of the six samples had not failed when run-off testing was halted after the 23rd test.
[17]Octylphenoxypoylethoxyethanol having 12-13 ethylene oxide groups, obtained from the Rohm and Haas Co.
[18]Average of six runs rounded off to the nearest whole number.

While the invention has been described in detail with respect to specific embodiments thereof, it will be appreciated that those skilled in the art, upon attaining an understanding of the foregoing, may readily conceive of alterations to and variations of these embodiments. Such alterations and variations are believed to fall within the scope and spirit of the invention and the appended claims.

What is claimed is:

1. A method of treating a low hydrohead fibrous porous web to improve the web's retentive wettability by increasing, by at least about 50%, as compared to untreated web material, the average number of run-off tests that the low hydrohead web material can sustain without unacceptable run-off, the method comprising:
   providing a low hydrohead fibrous porous web material;
   forming a surface concentration on the web material of at least about 0.05%, by weight of the web material, of a surface active agent having a hydrophile-lipophile balance of at least about 6; and
   applying a corona discharge equivalent to a charge of at least about 0.6 watt minute per square foot per side of the web material to the surface active agent bearing web material.

2. The method of claim 1, wherein the surface concentration of the surface active agent is from about 0.05% to about 3%, by weight of the web material.

3. The method of claim 1, wherein the surface concentration of the surface active agent is from about 0.1% to about 1%, by weight of the web material.

4. The method of claim 1, wherein the surface concentration of the surface active agent is from about 0.1% to about 0.4%, by weight of the web material.

5. The method of claim 1, wherein the surface concentration of the surface active agent is from about 0.2% to about 0.3%, by weight of the web material.

6. The method of claim 1, wherein the equivalent of from about 0.6 to about 10 watt minute per square foot per side of the web material of corona discharge is applied to the web material.

7. The method of claim 1, wherein the equivalent of from about 1 to about 5 watt minute per square foot per side of the web material of corona discharge is applied to the web material.

8. The method of claim 1, wherein the equivalent of from about 2 to about 4 watt minute per square foot per side of the web material of corona discharge is applied to the web material.

9. The method of claim 1, wherein the hydrohead of the web material is less than 20 centimeters of water.

10. The method of claim 1, wherein the hydrohead of the web material is about 15 centimeres of water.

11. The method of claim 1, wherein the number of run-off tests prior to unacceptable run-off is increased by at least about 100%.

12. The method of claim 1, wherein the number of run-off tests prior to unacceptable run-off is increased by at least about 200%.

13. The method of claim 1, wherein the surface active agent is selected from the group consisting of one or more wetting agents, emulsions and detergents.

14. The method of claim 1, wherein the surface active agent is a wetting agent.

15. The method of claim 1, wherein the surface active agent is a surfactant.

16. The method of claim 1, wherein the surface active agent is an emulsion.

17. The method of claim 1, wherein the surface active agent is a detergent.

18. The product prepared by the process of claim 1.

19. A method of treating a low hydrohead fibrous porous web to improve the web's retentive wettability by increasing, by at least about 50%, as compared to untreated web material, the average number of run-off tests that the low hydrohead web material can sustain without unacceptable run-off, the method comprising:
  providing a low hydrohead fibrous porous web material;
  forming a surface concentration on the web material of from at least about 0.1% to about 1%, by weight of the web material, of a surface active agent having a hydrophile-lipophile balance of from 10 to 20; and
  applying a corona discharge equivalent to a charge of from at least about 1 to 5 watt minute per square foot per side of the web material to the surface active agent bearing web material.

20. The method of claim 1, wherein the hydrophile-lipophile balance of the surface active agent ranges from 8 to about 20.

21. The method of claim 1, wherein the hydrophile-lipophile balance of the surface active agent ranges from 10 to about 20.

22. The method of claim 1, wherein the hydrohead of the web material is less than about 25 centimeters of water.

23. A method of treating a low hydrohead fibrous porous web to improve the web's retentive wettability by increasing, by at least about 50%, as compared to untreated web material, the average number of run-off tests that the low hydrohead web material can sustain without unacceptable run-off, the method comprising:
  providing a low hydrohead fibrous porous web material;
  forming a surface concentration on the web material of from at least about 0.05% to about 3%, by weight of the web material, of a surface active agent having a hydrophile-lipophile balance of from 8 to 20; and
  applying a corona discharge equivalent to a charge of from at least about 0.6 to 10 watt minute per square foot per side of the web material to the surface active agent bearing web material.

24. The product prepared by the process of claim 23.

* * * * *